United States Patent [19]

Degner et al.

[11] 4,441,970

[45] Apr. 10, 1984

[54] ELECTROCHEMICAL PREPARATION OF 2,5-DIALKOXY-2,5-DIHYDROFURANS

[75] Inventors: Dieter Degner, Dannstadt-Schauernheim; Heinz Hannebaum, Ludwigshafen, both of Fed. Rep. of Germany

[73] Assignee: BASF Aktiengesellschaft, Ludwigshafen, Fed. Rep. of Germany

[21] Appl. No.: 435,037

[22] Filed: Oct. 18, 1982

[30] Foreign Application Priority Data

Oct. 28, 1981 [DE] Fed. Rep. of Germany ....... 3142626

[51] Int. Cl.³ ............................................... B01D 3/34
[52] U.S. Cl. ................................................. 204/59 R
[58] Field of Search ................................ 204/59 R, 78

[56] References Cited

FOREIGN PATENT DOCUMENTS 2710420  8/1978  Fed. Rep. of Germany .

OTHER PUBLICATIONS

Dieter et al., 90: 94451f., (1979).
Krishan, V., et al., 91: 183932b, (1979).
Stibor, I., et al., 83: 170090k, (1975).
Krishnan et al., Trans. SAEST 1979, 14(1), 39–42.

*Primary Examiner*—John F. Niebling
*Attorney, Agent, or Firm*—John H. Shurtleff

[57] ABSTRACT

2,5-Dialkoxy-2,5-dihydrofurans are prepared by a process in which 2,5-dihydrofuran is oxidized electrochemically in the presence of an alkanol.

14 Claims, No Drawings

ELECTROCHEMICAL PREPARATION OF 2,5-DIALKOXY-2,5-DIHYDROFURANS

The present invention relates to a novel electrochemical process for the preparation of 2,5-dialkoxy-2,5-dihydrofurans from 2,5-dihydrofuran and an alkanol.

2,5-Dialkoxy-2,5-dihydrofurans can be prepared by a process described in Organic Syntheses 40 (1960), 29, by reacting furan with bromine in alcoholic solution at below −20° C. The disadvantage of this synthesis is that it requires very substantial amounts of bromine and bases, which result in considerable pollution of the effluent. A further disadvantage industrially is the low temperature required. These disadvantages can be avoided if the 2,5-dialkoxy-2,5-dihydrofurans are prepared by electrochemical oxidation of furan. A process which is very suitable for industrial use is described in German Published Application DAS No. 2,710,420. However, furan, which requires very expensive safety measures when handled industrially, is employed as a starting material in this process too.

We have found that 2,5-dialkoxy-2,5-dihydrofurans of the general formula

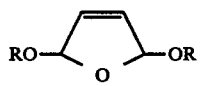

I where R is alkyl of 1 to 4 carbon atoms, can be prepared in a particularly simple manner by a process in which 2,5-dihydrofuran is oxidized electrochemically in the presence of an alkanol of the formula ROH.

2,5-Dihydrofuran is very readily obtainable by splitting off water from butene-1,4-diol, and is substantially easier to handle industrially than furan. It is surprising that the 2,5-dialkoxy-2,5-dihydrofurans can be prepared so readily from 2,5-dihydrofuran using the process according to the invention, since J.Am.Chem.Soc. 94 (1972), 7,892 discloses that olefins, when oxidized electrochemically, give only very poor material yields and current efficiencies in many cases. In particular, the regioselective introduction of two alkoxy groups in the novel process is very surprising.

Using the synthesis of 2,5-dimethoxy-2,5-dihydrofuran as an example, the novel process can be illustrated in more detail by the following equation:

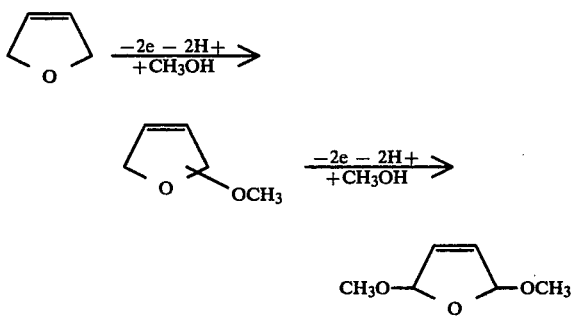

In this synthesis, monomethoxydihydrofuran is an intermediate, and the novel process may therefore also be carried out using, instead of 2,5-dihydrofuran, a monoalkoxydihydrofuran of the general formula

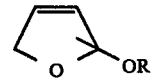

II where R has the above meaning.

The novel process does not require any special electrolysis cells, and may be carried out in the conventional industrial compartmented and non-compartmented cells. The electrochemical oxidation of 2,5-dihydrofuran is preferably carried out using an electrolyte which consists of this compound, an alkanol and a conducting salt. Examples of alkanols which may be used are methanol, ethanol, n-propanol and isopropanol, but methanol is preferred.

The conducting salt employed in the novel process dissolves in the 2,5-dihydrofuran/alkanol mixture and imparts conductivity to the solution. Examples of such conducting salts are halides, eg. KF and NaBr, alcoholates, eg. $NaOCH_3$, salts of alkanoic acids, eg. potassium acetate, sulfonates, eg. potassium benzenesulfonate and tetraethylammonium p-toluenesulfonate, alkyl sulfates, eg. tetramethylammonium methosulfate, tetrafluoborates, eg. $LiBF_4$, and hexafluorophosphates, eg. $KPF_6$. Mixtures of these conducting salts, or even bases, eg. KOH, may also be employed. Halides, sulfonates or alcoholates are preferably employed as conducting salts in the novel process, potassium benzenesulfonate being particularly preferred.

The electrolyte composition can be varied within wide limits, and may be, for example, as follows: from 5 to 50% by weight of 2,5-dihydrofuran, from 1 to 10% by weight of conducting salt and from 40 to 94% by weight of alkanol.

Materials which are stable under the conditions of electrolysis are employed for the anode, examples of such materials being noble metals, eg. platinum, oxides, eg. ruthenium dioxide on titanium, graphite and glass-like carbon. Platinum anodes and graphite anodes are preferably employed. Examples of cathode materials which may be used are metals, eg. iron, metal alloys, eg. steel, noble metals, eg. platinum, and graphite.

The current density may likewise be varied within wide limits, and is, for example, from 1 to 30 $A/dm^2$, preferably from 2 to 15 $A/dm^2$. The electrolysis temperature is restricted by the boiling point of the 2,5-dihydrofuran, and is therefore advantageously below 60° C.

The conversion of 2,5-dihydrofuran may be chosen within wide limits, but is preferably above 50%. Unreacted 2,5-dihydrofuran, together with any monomethoxydihydrofuran still present, can be recycled to the electrolysis.

The material issuing from the electrolysis is worked up by a conventional method. Thus, the excess alcohol, together with any 2,5-dihydrofuran still present, is distilled off under atmospheric pressure and the distillate obtained is recycled to the electrolysis. The conducting salt, which remains in the bottom product, is separated off from the crude dialkoxydihydrofuran, for example by filtration, and may likewise be recycled to the electrolysis. The 2,5-dialkoxy-2,5-dihydrofurans can be purified further, for example by rectification. The novel process may be carried out either batchwise or continuously.

EXAMPLES 1 TO 4

A non-compartmented electrolysis cell containing a stack of plates was used in all Examples. The stack comprised from 6 to 11 electrodes, with spacings of 0.5 mm. During electrolysis, which was carried out batchwise, the electrolyte was pumped through a heat exchanger at a rate of 200 liters/hour. The material issuing from the electrolysis was worked up by distillation. First, methanol, together with any 2,5-dihydrofuran still present, was distilled off under atmospheric pressure, and thereafter the conducting salt was filtered off from the crude 2,5-dimethoxy-2,5-dihydrofuran, and the latter was purified by distillation at 80°–100° C. and 120–150 mbar.

The purity was determined by gas chromatography. Details of the experiments, and the results, are summarized in the Table below.

| | | | | Electrolysis | | | | | Conver- | | |
|---|---|---|---|---|---|---|---|---|---|---|---|
| | | | Current | using Q | | | | | sion of | | |
| Ex- | Electrode | Electrolyte | density | (F/mole of | T | DHF | MDF | DMD | DHF | MY | CE |
| ample | material | (g) | (A/dm²) | DHF) | (°C.) | (g) | (g) | (g) | (%) | (%) | (%) |
| 1 | A: graphite<br>C: graphite | 280 DHF<br>21.4 KSO₃C₆H₅<br>2,291 CH₃OH | 4 | 4 | 25–27 | 7.7 | — | 342.3 | 97.3 | 67.7 | 65.8 |
| 2 | A: graphite<br>C: graphite | 280 DHF<br>25 NaOCH₃<br>2,251 CH₃OH | 2–4 | 4 | 25–27 | 15.6 | 42.0 | 230.9 | 94.4 | 52.9 | 49.7 |
| 3 | A: graphite<br>C: graphite | 280 DHF<br>25 KOAc<br>2,251 CH₃OH | 2–4 | 4 | 22–29 | 28.7 | 44.4 | 177.1 | 89.8 | 43.3 | 39.6 |
| 4 | A: graphite<br>C: graphite | 280 DHF<br>25 KF<br>2,370 CH₃OH | 4 | 3 | 25–27 | 122.1 | 71.6 | 156.6 | 56.4 | 78.2 | 52.1 |

T: Electrolysis temperature

DHF: 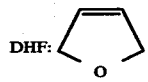

MDF: 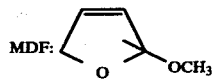

DMD: 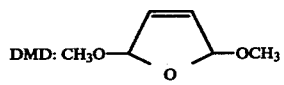

A: Anode
C: Cathode
MY: Material yield
CE: Current efficiency

We claim:
1. A process for the preparation of a 2,5-dialkoxy-2,5-dihydrofuran of the formula

  I where R is alkyl of 1 to 4 carbon atoms, which comprises:
electrochemically oxidizing 2,5-dihydrofuran in an electrolyte containing an alkanol of the formula ROH.

2. A process as claimed in claim 1, wherein the alkanol used is methanol.

3. A process as claimed in claim 1, wherein the electrochemical oxidation is carried out on a graphite or platinum anode.

4. A process as claimed in claim 2, wherein the electrochemical oxidation is carried out on a graphite or platinum anode.

5. A process as claimed in claim 1, wherein the electrolyte contains as a conducting salt an alcoholate, a sulfonate, a halide or mixtures thereof.

6. A process as claimed in claim 2, wherein the electrolyte contains as a conducting salt an alcoholate, a sulfonate, a halide or mixtures thereof.

7. A process for the preparation of a 2,5-dialkoxy-2,5-dihydrofuran of the formula

  I where R is alkyl of 1 to 4 carbon atoms, which comprises:
electrochemically oxidizing a monoalkoxydihydrofuran of the formula

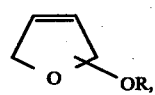  II where R has the meaning given above, in an electrolyte.

8. A process as claimed in claim 7, wherein R is methyl.

9. A process as claimed in claim 7, wherein the electrolyte contains as a conducting salt an alcoholate, a sulfonate, a halide or mixtures thereof.

10. A process as claimed in claim 8, wherein the electrolyte contains as a conducting salt an alcoholate, a sulfonate, a halide or mixtures thereof.

11. A process as claimed in claim 1 wherein the electrochemical oxidation is carried out at a current density of from 1 to 30 A/dm$^2$.

12. A process as claimed in claim 2 wherein the electrochemical oxidation is carried out at a current density of from 2 to 15 A/dm$^2$.

13. A process as claimed in claim 7 wherein the electrochemical oxidation is carried out at a current density of from 1 to 30 A/dm$^2$.

14. A process as claimed in claim 8 wherein the electrochemical oxidation is carried out at a current density of from 2 to 15 A/dm$^2$.

* * * * *